United States Patent [19]
Sterling et al.

[11] Patent Number: 5,880,157
[45] Date of Patent: Mar. 9, 1999

[54] DERIVATIVES OF TETRAMETHYLCYCLOPROPANE

[75] Inventors: Jeff Sterling, Jerusalem; Yaacov Herzig, Raanana; Meir Bialer, Jerusalem; Abdullah Haj-Yehia, Jerusalem; Boris Yagen, Jerusalem, all of Israel

[73] Assignee: Yissum Research Development Company of the Hebrew University of Jerusalem, Jerusalem, Israel

[21] Appl. No.: 687,486

[22] PCT Filed: Feb. 8, 1995

[86] PCT No.: PCT/US95/01388

§ 371 Date: Nov. 25, 1996

§ 102(e) Date: Nov. 25, 1996

[87] PCT Pub. No.: WO95/21814

PCT Pub. Date: Aug. 17, 1995

[30] Foreign Application Priority Data

Feb. 8, 1994 [IL] Israel ........................................ 108595

[51] Int. Cl.$^6$ ........................ A61K 31/16; C07C 231/02; C07C 233/58
[52] U.S. Cl. .......................... 514/624; 514/616; 564/138; 564/139; 564/152; 564/155; 564/190
[58] Field of Search ..................................... 564/190, 152, 564/138, 139, 155; 514/624, 616

[56] References Cited

U.S. PATENT DOCUMENTS

| | | |
|---|---|---|
| 4,291,055 | 9/1981 | Chen . |
| 4,411,925 | 10/1983 | Brennan et al. ......................... 426/548 |
| 4,710,518 | 12/1987 | Kurahashi et al. ...................... 514/624 |
| 4,959,493 | 9/1990 | Ohfume et al. . |

FOREIGN PATENT DOCUMENTS

| | | |
|---|---|---|
| 0069811 | 1/1983 | European Pat. Off. . |
| 2732811 | 1/1978 | Germany . |
| 53-10977 | 4/1978 | Japan . |
| 60-224663 | 11/1985 | Japan . |

OTHER PUBLICATIONS

Haj–Yehia et al., Journal of Pharmaceutical Sciences, vol. 79, No. 8, pp. 719–724 (1990).

Graham et al., Journal of Medicinal Chemistry, vol. 30, No. 6, pp. 1074–1090 (1987).

*Primary Examiner*—Shailendra Kumar
*Attorney, Agent, or Firm*—Birch, Stewart, Kolasch & Birch, LLP

[57] ABSTRACT

The present invention relates to derivatives of 2,2,3,3-tetramethylcyclopropane carboxylic acid (TMCA) of general formula (I), $$\text{(I)}$$

wherein R is lower alkyl group ($C_1$–$C_6$), an aryl group, an aralkyl group or an amide of general formula (II), $$-\underset{R_1}{\underset{|}{CH}}-(CH_2)_n-\overset{O}{\overset{\|}{C}}-NHR_2 \quad \text{(II)}$$

where $R_1$ and $R_2$ are the same or different and may be hydrogen, a alkyl group ($C_1$–$C_6$), an aryl group or an aralkyl group, and n=0–3, to their racemic mixtures and the D and L enantiomers. The invention also relates to processes for the preparation of said compounds and for pharmaceutical preparations comprising the same. The new compounds show improved activity against epilepsy.

24 Claims, No Drawings

DERIVATIVES OF TETRAMETHYLCYCLOPROPANE

This application is a 371 of PCT/US95/01388, filed Feb. 8, 1995, WO95/21814, Aug. 17, 1995.

The present invention relates to derivatives of tetramethyl-cyclopropane carboxylic acid amides, their preparation and pharmaceutical compositions comprising them.

Valporic acid (VPA) and its alkali salts are major drugs in the arsenal of drugs for the treatment of epileptic seizures and convulsions. However, approximately 25% of epileptic patients do not respond to current treatment. Furthermore, VPA has considerable adverse side effects including hepatoxicity and teratogenicity. (See Baille, T. A. et al. In Antiepileptic Drugs, eds. R. H. Levy et al. Raven Press, New York. pp. 641–651 (1989)). One approach to obtain improved antiepileptic agents was to study the primary amide derivatives of VPA and its analogs. (See Bialer, M. Clin. Pharmacokinet. 20:114–122 (1991), Bialer, M. et al. Eur.J.-Clin.Pharmacol. 289–291 (1990), Haj Yehia, A. and Bialer M. J. Pharm.Sci. 79:719–724 (1990)). In addition, glycinamides have been described for this purpose in U.S. Pat. No. 4,639,468. However, these compounds are not generally accepted clinically. Thus, there is still a great need for anticonvulsant agents with an improved efficacy, and agents which give a better margin between the therapeutic dose and the dose which is neurotoxic.

The present invention consists in derivatives of 2,2,3,3-tetramethylcyclopropane carboxylic acid (TMCA) of general formula I,

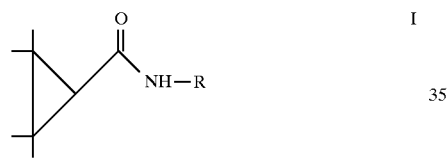

wherein R is a lower alkyl group ($C_1$–$_6$) an aryl group, an aralkyl group or an amide of general formula II,

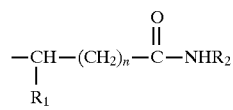

where $R_1$ and $R_2$ are the same or different and may be a hydrogen, a lower alkyl group ($C_1$–$C_6$), an aryl group or an aralkyl group, and n=0–3

Some of the compounds of this invention possess chiral centres. Both the racemic mixtures and the D and L enantiomers are within the scope of the present invention.

The new compounds according to the present invention show improved activity over known antiepileptic agents. Said compounds of the invention are highly effective in at least two generally accepted models of epilepsy: the maximal electroshock test (MES), which is indicative of generalized and partial seizures; and the subcutaneous pentylenetetrazole test (sc Met), which is indicative of absence seizures. Furthermore, the median effective dose ($ED_{50}$) of the agents claimed in this disclosure are considerably lower than those required to produce neurological impairment. Our results in animal models indicate that compounds in this group are effective against generalized and partial seizures, in addition to absence seizures and other forms of epilepsy.

The preferred compounds of the present invention are the following:

2,2,3,3-tetramethylcyclopropanecarboxamide
N-methyl-2,2,3,3-tetramethylcyclopropanecarboxamide
N-phenyl-2,2,3,3-tetramethylcyclopropanecarboxamide
N-[(2,2,3,3-tetramethylcyclopropyl)carbonyl]-glycinamide
N-(2,2,3,3-tetramethylcyclopropyl)carbonyl)-alaninamide
N-(2,2,3,3-tetramethylcyclopropyl)carbonyl]-phenylalaninamide
N-(2,2,2,3-tetramethylcyclopropyl)carbonyl]-phenylglycinamicle
N-[(2,2,3,3-tetramethylcyclopropyl)carbonyl)-N'-benzyl-alaninamide
N-[(2,2,3, 3-tetramethylcyclopropyl)carbonyl]-4-aminobutyramide The compounds of general formula I, wherein R has the same meaning as defined above and may also stand for hydrogen, may be prepared, inter alia, as follows:

a) by reacting a solution of TMCA chloride in an inert organic solvent with a suitable amine at a temperature range of 0°–60° C. for a period of 1 to 36 hours.

The inert organic solvent may be, for example, tetrahydrofuran (THF), $CH_2Cl_2$. The amines may be in any form, preferably as an aqueous solution thereof. The temperature is preferably 20°–40° C. and the time of the reaction 4–24 hours. All temperatures are indicated here in degrees Celsius; or b) by reacting an ester of TMCA with an amine of the formula $RNH_2$. This reaction may be performed, for example, with N-hydroxysuccinimide, in the presence of carbodiimides, e.g. dicyclohexylcarbodiimide (DCC) or N-(dimethylaminopropyl)-N'-ethyl (DMAPE) carbodiimide, at a temperature ranging from 0°–50° C., preferably at 0°–25° C., in an inert solvent, e.g. tetrahydrofuran (THF), dioxane, 1,2-dimethoxyethane, $CH_2Cl_2$, dimethyl formamide (DMF); the activated ester, either in its isolated form or in situ, is then reacted with $RNH_2$ under the same conditions as detailed above.

Said methods are illustrated as follows:

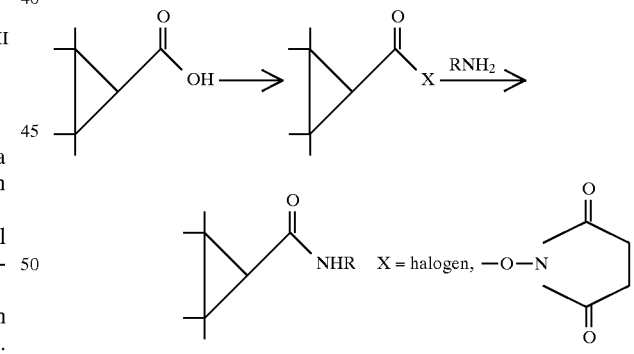

When R is not of general formula II, method (a) is preferred When R is of general formula II, method (b) is preferred and the amine ($RNH_2$) is an amino acid amide.

The compounds of the general formula wherein R or $R_2$ are hydrogen, may be used either as free bases or as their addition salts, e.g. HCl salts. Generally, the compounds of formula I may be either in their enantiomeric form or as racemic mixtures.

The enantiomer may be prepared by selecting the corresponding amino acid isomer in the course of the process for the preparation given herein.

The present invention consists also in a pharmaceutical composition comprising a compound of general formula I, as defined above, in which R may also stand for hydrogen, or a pharmaceutically acceptable salt thereof, where appropriate, in a therapeutically effective amount and a pharmaceutically acceptable carrier.

In the practice of the invention, the amount of the compound incorporated in the pharmaceutical composition may vary widely. Factors considered when determining the precise amount as well known to those skilled in the art. Examples of such factors include, but are not limited to, the subject being treated, the specific pharmaceutical carrier, and route of administration being employed and the frequency with which the composition is to be administered. A pharmaceutical composition in unit dose form for treatment of the disorders listed hereinabove comprises, advantageously, 10 to 500 mg of the active ingredient.

In a preferred embodiment, the compound is administered in a pharmaceutical composition which comprises the compound and a pharmaceutically acceptable carrier. As used herein, the term "pharmaceutically acceptable carrier" encompasses any of the standard pharmaceutically accepted carriers, such as a phosphate-buffered saline solution, water, emulsions such as an oil/water emulsion or a triglyceride emulsion, various types of wetting agents, tablets, coated tablets, and capsules. An example of an acceptable triglyceride emulsion useful in the intravenous and intraperitoneal administration of the compounds is the triglyceride emulsion commercially known as Intralipid.

Typically, such carriers contain excipients such as starch, milk, sugar, certain types of clay, gelatin, stensic acid, talc, vegetable fats or oils, gums, glycols, or other known excipients. Such carriers may also include flavor and color additives or other ingredients.

In the practice of the invention, the administration of the pharmaceutical composition may be effected by any of the well known methods including, but not limited to, oral, intravenous, intraperitoneal, intramuscular or subcutaneous or topical administration. Topical administration can be effected by any method commonly known to those skilled in the art and include, but are not limited to, incorporation of the pharmaceutical composition into creams, ointments, or transdermal patches.

The present invention also consists in the use of compounds of general formula I, as herein defined, wherein R may also stand for hydrogen in the treatment of epilepsy.

The present invention will now be illustrated with reference to the following Examples without being limited by same.

EXAMPLE 1

N-Methyl-2,2,3,3-tetramethylcyclopropanecarboxamide. (Compound 1)

A solution of 2,2,3,3-tetramethylcyclopropanecarbonyl chloride (16.05 g, 0.1 mole) in the THF (50 ml) was added slowly to 35% aqueous methyl amine (200 ml). The reaction mixture was stirred for 24 hours at room temperature, and, after removal of THF under reduced pressure, was extracted with $CH_2Cl_2$ (2×50 ml). The $CH_2Cl_2$ extract was washed successively with $H_2O$ (2×100 ml), 0.3 N HCl (200 ml), 0.1 $NaHCO_3$ (100 ml) and saturated NaCl (150 ml), dried over $MgSO_4$ and evaporated to dryness under reduced pressure. The crude product was treated with hexane (100 ml) at room temperature for 30 minutes, filtered and dried to afford 10.5 g (68 mmole, 68%) of a white solid, m.p.: 98° C.

Anal. calculated for $C_9H_{17}NO$:

Calculated: C: 69.62% H: 11.04% N: 9.03%

Found: C: 68.90% H: 10.89% N: 9.72%

$^1$H NMR δ($CDCl_3$): 5.55 (br s, 1H, NH), 2.78 (d,3H, NH Me), 1.27 (s,

6H, Me), 1.15 (s, 6H, Me), 0.83 (s, 1H CH) ppm

MS: 156 ($MH^+$,100).

IR(KBr): 3268, 1641, 1562, 1423, 1252, 1119 $cm^{-1}$.

EXAMPLE 2

(Compound 3)

2,2,3,3-Tetramethylcyclopropanecarboxamide

The compound was obtained from 2,2,3,3-tetramethylcyclopropane-carbonyl chloride and aqueous ammonia, by the same procedure as described in Example 1. Crystallization ($CHCl_3$:hexane) afforded 7.05 g (50 mmole, 50%) of a crystalline white solid.

Anal. calculated for $C_8H_{15}NO$:

Calculated: C: 68.0% H: 10.0% N: 9.9%

Found: C: 66.7% H: 10.3% N: 9.2%

EXAMPLE 3

N-Phenyl-2,2,3,3-tetramethylcyclopropanecarboxamide

A solution of 2,2,3,3-tetramethylcyclopropanecarbonyl chloride (1.60 g, 10 mmole) in $CH_2Cl_2$ (5 ml) was added dropwise to a solution of aniline (2.8 g, 30 mmole) in $CH_2Cl_2$ (10 ml), while maintaining the temperature at 10°–20° C. The reaction mixture was stirred for 6 hours at room temperature, diluted with $CH_2Cl_2$ (15 ml) and washed successively with $H_2O$ (2×10 ml), 1N HCl (2×10 ml), $H_2O$ (20 ml) saturated NaCl (2×15 ml). The organic layer was separated, dried over $MgSO_4$, and evaporated to dryness under reduced pressure. The residue was crystallized from EtOAc/hexane to afford 1.1 g (5.07 mmole, 51%) of a white crystalline solid), m.p. 149° C.

Anal. calculated for $C_{14}H_{19}NO$:

Calculated: C: 77.37% H: 8.82% N: 6.45%

Found: C: 77.65% H: 8.57% N: 6.55%

1H NMR δ(CDC13): 7.48, 7.29, 7.05 (5H, Ph) 7.20 (br s 1H, NH), 1.33 (s, 6H, Me), 1.22 (s, 6H, Me), 1.00 (s, 1H, CH) ppm

MS: 218 ($MH^+$, 100).

IR (KBr): 3300, 2930, 1656, 1600, 1533, 1502, 1444, 1203, 1114 $cm^{-1}$.

EXAMPLE 4

(Compound 2)

N-[(2,2,3,3-Tetramethylcyclopropyl)carbonyl]-glycinamide

To a solution of TMCA (2.82 g, 20 mmole) in dry $CH_2Cl_2$ (150 ml) were added N-hydroxysuccinimide (2.3 g, 20 mmole) and DMAPE-carbodiimide.HCl (3.92 g, 20 mmole). The substance obtained was stirred for 15 hours at room temperature. To this mixture was added $(CH_3CH_2)_3N$ (4.5 ml), glycinamide.Hcl (2.2 g. 20 mmole) and dry DMF (100 ml), and stirred for 24 hours at room temperature. The solvents were stripped off under reduced pressure. The residue was purified by chromatography ($SiO_2$, $CHCl_3$:MeOH 97:3) followed by successive crystallization from $CH_2Cl_2$:hexane and EtOAc:hexane, to afford 1.1 g (5.6 mmole, 28%) of a white crystalline solid, m.p.: 176° C.

Anal. calculated for $C_{10}H_{18}N_{2l\ o2}$:

Calculated: C: 60% H: 9.1% N: 14%

Found: C: 60.4% H: 8.9% N: 14.1%

$^1$H NMR δ($CDCl_3$): 6.2 (br. s, 2H, NH), 5.40 (br. s, 1H, NH), 3.93 (d, 2H, $CH_2$), 1.26 (s, 6H, Me), 1.17 (s, 6H, Me), 0.95 (s, 1H, CH) ppm MS: 199 (MH+, 100).

EXAMPLE 5

N-[2,2,3,3-Tetramethylcyclopropyl)carbonyl]-phenylalaninamide

To an ice-cooled solution of N-hydroxysuccinimide (2.85 g, 24.75 mmole) in anhydrous 1,2-dimethoxyethane (DME, 35 ml) were added TMCA (3.20 g, 22.5 mmole) and DCC (5.41 g, 26.25 mmole). The reaction mixture was stirred for 1 hour at 0–5° C. and for 20 hours at ambient temperature, and filtered. To this filtrate was added a suspension of L-phenylalaninamide (3.69 g, 22.5 mmole) and $(CH_3CH_2)_3N$ (2.27 g, 22.5 mmole) in DME (15 ml). The reaction mixture was stirred for 20 hours at room temperature, filtered, and the cake washed with DME (20 ml). The combined filtrates were evaporated to dryness under reduced pressure, and the residue was taken up in EtOAc (100 ml) and water (100 ml). The organic phase was separated, washed successively with 0.1 N $NaHCO_3$ (2×90 ml), 0.3 N HCl (100 ml) and saturated NaCl (2×75 ml), dried over $MgSO_4$ and evaporated to dryness under reduced pressure. The crude product was purified by column chromatography ($SiO_2$, $CH_2Cl_2$:MeOH 97:3) followed by crystallization from EtOAc/hexane, to afford 3.15 g (10.9 mmole, 48w) of a white cystalline solid, m.p.: 128° C.

Anal. calculated for $C_{17}H_{24}N_2O_2$:

Calculated: C: 70.79% H: 8.39% N: 9.72%

Found: C: 70.49% H: 8.64% N: 9.79%

$^1$H NMR δ(CDC13): 7.26 (m, 5H, Ph), 6.12 (br d, 1H, NH), 6.07 (br s, 1H, $CONH_2$), 5.48 (br s, 1H, $CONH_2$), 4.70 (q, 1H, $C_\alpha$H), 3.06 (d, 2H, $CH_2$Ph), 1.21 (s, 3H, Me), 1.15 (s, 3H, Me), 1.13 (s, 6H, Me), 0.85 (s, 1H, CH) ppm

MS: 289 ($MH^+$, 100), 272 ($MH^+$—$NH_3$, 42), 125 (

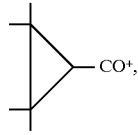

15).

IR (KBr): 3360, 3190, 2900, 1676, 1626, 1526, 1424, 1379, 1233 1119 $cm^{-1}$

EXAMPLE 6

N-[(2,2,3,3-Tetramethylcyclopropyl)carbonyl]-alaninamide

The compound was prepared from TMCA (2.13 g, 15 mmole) and alaninamide.HCl (1.87 g, 15 mmole) by the same procedure as described in Example 5, except that a 50% molar excess of $(CH_3CH_2)_3N$ was used. The crude product was crystallized from EtOAc to afford 1.1 g (5.19 mmole, 35%) of a white crystalline solid, m.p.: 178° C.

Anal. calculated for $C_{11}H_{20}N_2O_2$:

Calculated: C: 62.2% H: 9.50% N: 13.20%

Found: C: 61.91% H: 9.55% N: 13.14%

$^1$H NMR δ($CDCl_3$): 6.65 (br s, 1H, $CONH_2$), 6.17 (br d, 1H, NH), 5.58 (br S, 1H, $CONH_2$) 4.55 (qt, 1H $C_\alpha$—H), 1.38 (d, 3H, Ala— Me), 1.25 (s, 3H, Me), 1.22 (s, 3H, Me), 1.16 (s, 3H, Me), 1.15 (s, 3H, Me), 0.91 (s, 1H, CH) ppm.

MS: 213 ($MH^+$, 18), 196 ($MH^+$—$NH3$, 34), 125 (

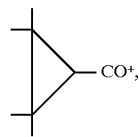

100).

IR (KBr): 3330, 3270, 3150, 3000, 1694, 1638, 1543, 1460, 1252, 1138 $cm^1$.

EXAMPLE 7

N-[(2,2,3,3-Tetramethylcyclopropyl)carbonyl]-phenylglycinamide

The compound was prepared from phenylglycinamide and TMCA in a manner analogous to that described in Example 5. The crude product was purified by column chromatography ($SiO_2$, CH2cl2:MeOH 97:3) followed by crystallization from EtOAc/EtOH (100:3), to afford 1.5 g (5.5 mmoles, 18%) of a white crystalline solid, m.p.: 2280C.

Anal. calculated for C16H22N202:

Calculated: C: 70.03% H: 8.09% N: 10.21%

Found: C: 71.2% H: 8.05% N: 10.12%

1H NMR 6 (CDC13+CD30D): 7.35 (m, 5H, Ph), 5.44 (s, 1H, Ca—H), 1.23 (s, 3H, Me), 1. 174 (s, 3H, Me), 1. 168 (s, 3H Me), 1.15 (s, 3H, Me), 1.02 (s, 1H, CH) ppm.

MS: 175 (MH', 100), 258 (MH'—$NH3$, 17), 125 (

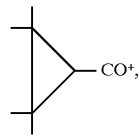

2).

IR (KBr): 3430, 3295, 2980, 1688, 1644, 1614, 1543, 1404, 1242, 1115 cm—1.

EXAMPLE 8

N-[2,2,3,3-Tetramethylcyclopropyl)carbonyl]-N'-benzylalaninamide a) Alaninebenzylamide was prepared from alanine methyl ester.HCl and benzylamine by a procedure based on that described in J.Med.Chem. 30, 567 (1987).

b) The above compound was then prepared from alaninebenzylamide prepared as described in (a) above (1.78 g, 10 mmole) and TMCA (1.42 g, 10 mmole) in a manner analogous to that described in Example 5.

The crude product was purified by column chromatography ($SiO_2$, $CH_2CL_2$:MeOH 97:3), followed by crystallization from hexane:EtOAc (75:25), to afford 1.4 g (4.64 mmole, 46%) of a white crystalline solid, m.p.: 129° C.

Anal. calculated for $C_{18}H_{26}N_2O_2$:

Calculated: C: 71.48% H: 8.67% N: 9.27%

Found: C: 71.76% H: 8.44% N: 9.21%

$^1$H NMR δ($CDCl_3$): 7.20–7.35 (m, 5H, Ph), 6.86 (br s, $PhCH_2NH$), 6.08 (br d, 1H,NH), 4.53 (m, 1H ala $C_\alpha$H), 4.40 (dd, 2H, $PhCH_2$), 1.34 (d 3H, ala $CH_3$), 1.22, 1.15, 1.14, 1.12 (4xs, 12H,Me), 0.90 (s 1H, CH) ppm.

MS: 303 ($MH^+$, 100), 196 ($MH^+$—$PhCH_2NH_2$, 5).

IR (KBr): 3300, 3063, 2980, 2924, 2870, 1673, 1640, 1453, 1378, 736, 699 $cm^{-1}$.

EXAMPLE 9

N-[2,2,3,3-Tetramethylcyclopropyl)carbonyl]-4-aminobutyramide a) A solution of 2,2,3,3-tetramethylcyclopropylcarbonyl chloride (8.45 g, 52 mmole) in toluene (100 ml) was added simultaneously with 4N NaOH (12.5 ml) to a vigorously stirred solution of GABA (5.15 g, 50 mmole) over a period of 20 minutes and the reaction mixture further stirred at room temperature for 1 hour. The toluene layer was removed and the aqueous phase was washed with $(CH_3CH_2)_2O$ (2×100 ml), cooled and acidified to pH=1. The precipitated white solid was collected, extensively washed with cold water and dried, to afford 8.8 g (38.8 mmole, 78%) of N-[2,2,3,3-tetramethylcyclopropyl)carbonyl]-GABA, m.p. 100°–2° C.

b) To a suspension of TMCA-GABA (8.8 g, 38.8 mmole) in toluene (200 ml) was added $SOCl_2$ (6.6 ml). The reaction mixture was refluxed for 3 hours and evaporated to dryness. The dark residue was dissolved in dioxane (35 ml), aq. $NH_4OH$ (50 ml) was then added, and the resulting solution was stirred at room temperature for 24 hours. The dark residue obtained after removal of solvents was taken up in hot EtOAc (430 ml), filtered and evaporated to dryness. The residual dark oil was purified by column chromatography $(SiO_2, CH_2Cl_2:MeOH$ 90:10) followed by crystallization (EtOAc) to afford 1.5 g (6.6 mmole, 13%) of the above compound as a whitish solid, m.p. 138°–9° C.

Microanal. calculated for $C_{12}H_{22}N_2O_2$:

Calculated: C: 63.68% H: 9.80% N: 12.38%

Found: C: 62.26% H: 9.39% N: 12.62%

$^1$H NMR δ(DMSO): 7.74 (br t, 1H, NH) , 7.25 (br s, 14, $CONH_2$), 6.73 (br S, IH, $CONH_2$), 3.0 (m, 2H, CONH $CH_2$, 2.05 (t, 2H, $CH_2CONH_2$), 1.60 (m, 2H $CH_2CH_2CONH_2$), 1.16 (s, 6H, Me), 1.10 (s, 6H, Me) ppm.

IR: 3300, 3170, 1682, 1643, 1557, 1250, 1190 $cm^{-1}$.

EXAMPLE 10

The following enantiomers were prepared by methods known in the art, by selecting the corresponding amino acid isomer in the appropriate process as described above: L-N-[(2,2,3,3-tetramethylcyclopropyl)carbonyl]-alaninamide, L-N-[(2,2,3,3-tetramethylcyclopropyl)carbonyl]-phenylalaninamide, DL-N-C(2,2,3,3-tetramethylcyclopropyl)carbonyl]-phenylglycinamide, and DL-N[2,2,3,3-tetramethylcyclopropyl)carbonyl]-N'-benzylalaninamide.

EXAMPLE 11

All compounds described before were screened for their ability to protect against seizures in two different models of epilepsy: the maximal electroshock seizure (MES) model; and the subcutaneous pentylenetetrazol (Metrazol) seizure threshold (s.c.Met) test. Agents effective in the MES model have been correlated with the ability to prevent the seizure spread, whereas those agents effective in the s.c. Met model have been correlated with the ability to raise the threshold for excitation of neural tissue. The $ED_{50}$ values in mg/kg of compounds 1, 2 and 3 as indicated in the Examples, are shown in Table 1. The PI value, the protective index, is calculated as described below.

TABLE 1

| | RATS | | | | MICE | | | |
|---|---|---|---|---|---|---|---|---|
| | MES | | scMet | | MES | | scMet | |
| COMPOUND | ED50 | PI | ED50 | PI | ED50 | PI | ED50 | PI |
| 1 | 82 | 2.0 | 45 | 3.6 | 98 | 0.8 | 39 | 2.1 |
| 2 | 82 | >6.1 | >250 | | 173 | 1.5 | 115 | 2.3 |
| 3 | >250 | | 52 | 7.3 | >120 | | 57 | 1.7 |
| Valproic Acid | 490 | 0.6 | 180 | 1.6 | 272 | 1.6 | 149 | 2.9 |
| ETS | >1200 | | 54 | 19 | >1000 | | 130 | 3.4 |

The three most commonly used drugs for generalized and partial epilepsy are Phenytoin, Carbamazepine and Valproic Acid. Compounds 1 and 2 both had a lower effective dose in the MES test (Table 1) ($ED_{50}$) for both mice and rats than Valproic Acid (VPA). The MES test is the most commonly used test to assess activity against these types of seizures. These results are therefore indicative of Compounds 1 and 2 having an efficacy against generalized and partial seizures. The most commonly used drugs for absence seizures are VPA and Ethosuximide (ETS). In the mouse model, Compounds 1, 2 and 3, all have effective doses in the s.c. Met test that were lower than that found for either VPA or ETS (Table 1). Since the s.c.Met test is the most commonly used test to indicate activity against absence seizures, the results are therefore indicative of Compounds 1, 2 and 3 having activity against absence seizures.

EXAMPLE 12

Neurotoxicity of the described compounds was assessed in mice (i.p. administration) by the rotorod ataxia test (See Swinyard et al., Supra, pages 85–100), and also in some cases in rats (p.o. administration) by the positional sense test and gait and stance test (see Swinyard above) . The $TD_{50}$ values in mg/kg are shown in Table 2.

TABLE 2

| | TD50 (mg/kg) | |
|---|---|---|
| COMPOUND | RATS | MICE |
| 1 | 163 | 83 |
| 2 | >500 | 259 |
| 3 | 381 | 99 |
| VALPROIC ACID | 281 | 426 |
| ETS | 1012 | 441 |

In all compounds where the median neurological toxic dose ($TD_{50}$) was quantitated in rats, the $TD_{50}$ was greater than the $ED_{50}$. The protective index values (PI, $PI=TD_{50}/ED_{50}$) therefore suggest that these compounds have a reasonable therapeutic dose range.

We claim:

1. Derivatives of 2,2,3,3-tetramethylcyclopropane carboxylic acid (TMCA) of formula I,

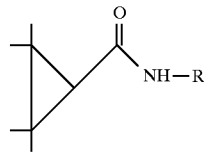

wherein R is a lower alkyl group ($C_1$–$C_6$), an unsubstituted aryl group, or an amide of formula II,

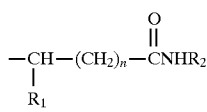

where $R_1$ and $R_2$ are the same or different and may be a hydrogen, a lower alkyl group ($C_1$–$C_6$), an aryl group or an aralkyl group, and n=0–3.

2. The racemic mixtures and the D and L enantiomers of compounds according to claim 1 which have chiral centers.

3. N-methyl-2,2,3,3-tetramethylcyclopropanecarboxamide.

4. N-phenyl-2,2,3,3-tetramethylcyclopropanecarboxamide.

5. N-[(2,2,3,3-tetramethylcyclopropyl)carbonyl]-glycinamide.

6. N-[(2,2,3,3-tetramethylcyclopropyl)carbonyl]-alaninamide.

7. N-[(2,2,3,3-tetramethylcyclopropyl)carbonyl]-phenylalaninamide.

8. N-[(2,2,3,3-tetramethylcyclopropyl)carbonyl]-phenylglycinamide.

9. N-[(2,2,3,3-tetramethylcyclopropyl)carbonyl]-N'-benzylalaninamide.

10. N-[(2,2,3,3-tetramethylcyclopropyl)carbonyl]-4-aminobutyramide.

11. A pharmaceutical composition comprising an effective anti-epileptic amount of a compound of formula I,

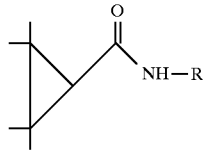

wherein R is a lower alkyl group ($C_1$–$C_6$), an unsubstituted aryl group or an amide of formula II,

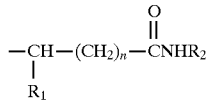

where $R_1$ and $R_2$ are the same or different and may be a hydrogen, a lower alkyl group ($C_1$–$C_6$), an aryl group or an aralkyl group, and n=0–3, or a pharmaceutically acceptable salt thereof, where appropriate, in a therapeutically effective amount; and a pharmaceutically acceptable carrier.

12. A pharmaceutical composition according to claim 11, comprising 10 to 500 mg of the active ingredient.

13. A process for the preparation of compounds of formula I according to claim 11, which comprises reacting a solution of TMCA chloride in an inert organic solvent with an amine at a temperature range of 0°–60° C. for a period of 1 to 36 hours.

14. A process according to claim 13 wherein the inert organic solvent is selected from the group consisting of tetrahydrofuran (THF) and $CH_2Cl_2$.

15. A process according to claim 13 or 14 wherein the amine is an aqueous solution.

16. A process according to claim 13 wherein the reaction temperature is 20°–24° C.

17. A process according to claim 13 wherein the reaction time is 4–24 hours.

18. A process for the preparation of the compound of formula I according to claim 11, which comprises reacting an ester of TMCA with an amino acid amide having the formula $RNH_2$, wherein R has the same meaning as in formula I.

19. A process according to claim 18, wherein R is a compound of formula II.

20. A process according to claim 18 or 19 which is performed with N-hydroxysuccinimide in the presence of carbodiimides, at a temperature range of 0°–50° C. in an inert solvent.

21. A process according to claim 20 in which the temperature range is 0°–25° C.

22. A process according to claim 20 wherein the carbodimide is selected from the group consisting of dicyclohexylcarbodiimide and N-(dimethylaminopropyl)-N'-ethyl carbodiimide.

23. A process according to claim 20, wherein the inert solvent is selected from the group consisting of THF, dioxane, 1,2-di-methoxyethane, $CH_2Cl_2$ and DMF.

24. A method of treating epilepsy comprising administering an effective amount of a composition, comprising:

a derivative of 2,2,3,3-tetramethylcyclopropane carboxylic acid (TMCA) of formula I,

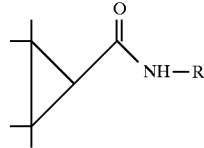

wherein R is a hydrogen, a lower alkyl group ($C_1$–$C_6$), an unsubstituted aryl group, or an amide of formula II,

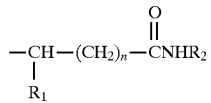

where $R_1$ and $R_2$ are the same or different and may be a hydrogen, a lower alkyl group ($C_1$–$C_6$), an aryl group or an aralkyl group, and n=0–3, and a pharmaceutically acceptable carrier therefor.

* * * * *